Figure 1:
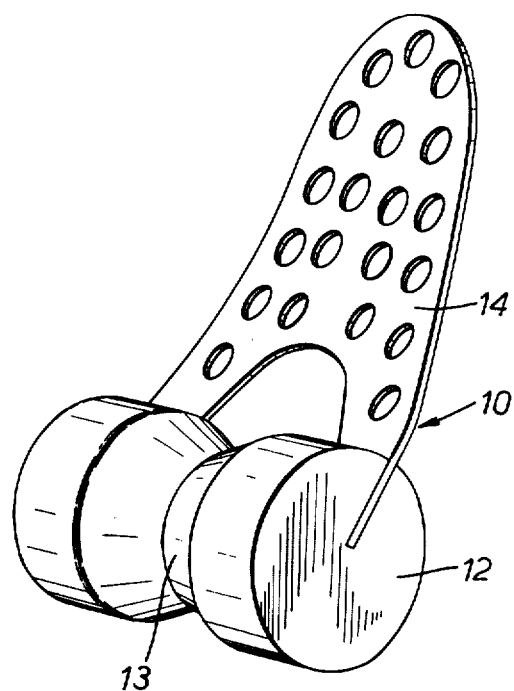

United States Patent [19]

Ring

[11] 4,038,704

[45] Aug. 2, 1977

[54] ELBOW PROSTHESIS

[75] Inventor: Peter Alexander Ring, Chaldon, England

[73] Assignee: Downs Surgical Limited, Mitcham, England

[21] Appl. No.: 694,341

[22] Filed: June 9, 1976

[30] Foreign Application Priority Data

June 11, 1975 United Kingdom ............... 25020/75

[51] Int. Cl.² .............................................. A61F 1/24
[52] U.S. Cl. ...................................... 3/1.91; 128/92 C
[58] Field of Search ............................ 3/1, 1.9–1.911; 128/92 C

[56] References Cited

U.S. PATENT DOCUMENTS

| 3,506,982 | 4/1970 | Steffee | 3/1.91 |
| 3,816,854 | 6/1974 | Schlein | 3/1.91 |
| 3,852,831 | 12/1974 | Dee | 3/1.91 |
| 3,869,730 | 3/1975 | Skobel | 3/1.91 |
| 3,919,725 | 11/1975 | Swanson et al. | 3/1.91 |

FOREIGN PATENT DOCUMENTS

| 2,064,432 | 7/1972 | Germany | 3/1.911 |

Primary Examiner—Ronald L. Frinks
Attorney, Agent, or Firm—Haight & Huard

[57] ABSTRACT

An elbow prosthesis comprising a humeral member and an ulnar member, in which each member comprises a joint portion for forming the joint of the prosthesis and an implant portion for implantation into the bone, the joint portion of the humeral member being capable of being received by the joint portion of the ulnar member in snap-fit engagement, while permitting the humeral member to pivot relative to the ulnar member.

15 Claims, 2 Drawing Figures

ELBOW PROSTHESIS

This invention relates to an elbow prosthesis.

Many different elbow and knee prostheses have been made and used. There is one fundamental difference between the requirements of knee prostheses and those of elbow prostheses: the forces normally exerted on the knee joint (for example, the weight of the body) act to push the two parts of a knee prothesis together, whereas the forces normally exerted on the elbow joint (for example, the weight of something held in the hand) act to pull the two parts of an elbow prosthesis apart. These factors have to be borne in mind in designing the two types of prostheses.

The present invention provides an elbow prosthesis comprising a humeral member and an ulnar member, in which each member comprises a joint portion for forming the joint of the prosthesis and an implant portion for implantation into the bone, the joint portion of the humeral member being capable of being received by the joint portion of the ulnar member in snap-fit engagement, while permitting the humeral member to pivot relative to the ulnar member.

The joint portion of the humeral member may be substantially cylindrical with a central annular neck portion capable of being received, in snap-fit engagement, by the joint portion of the ulnar member. Advantageously, the neck portion is in the shape of two coaxial frustocones abutting at their smaller ends.

The joint portion of the ulnar memeber may be substantially cuboid in shape with a recess extending from one side through to the opposing side, the recess being of substantially U-shaped cross-section in any plane parallel to the said two sides and capable of receiving the neck portion of the humeral member. The inner surfaces of the recess advantageously conform to the surfaces of the neck portion, and the width of the cuboid as measured between the said two sides is advantageously substantially the same as the longitudinal axial length of the neck portion.

The snap-fit engagement of the joint portion of the humeral member into the joint portion of the ulnar member can conveniently be arranged by having the depth of the recess in the ulnar member slightly greater than the radius of the corresponding part of the neck portion of the humeral member, such that the said substantially U-shaped cross-section is the major segment of a circle. In this way, the joint portion of the humeral member can be received in the said recess to slightly over half-way and is held in place by those parts of the joint portion of the ulnar member extending above a semi-circular shape.

The implant portion of the humeral member is advantageously rigidly joined to the joint portion of the humeral member. Preferably, it is substantially laminar and extends in a direction substantially at right angles to the pivotal axis of the prosthesis. The laminar implant portion may be substantially U-shaped or V-shaped in outline with its wider end secured to the said joint portion. It may be slightly curved in such a direction that a tangent to the curve extends substantially at right angles to the pivotal axis. This implant portion is preferably perforated, since bone can then grow through the perforations thus ensuring that the implant portion is rigidly fixed in the bone, optionally without the use of cement, which could become insecure after a while.

The implant portion of the ulnar member may be detachable from the joint portion of the ulnar member. Advantageously, it comprises a base plate with two lugs, preferably one at each end, extending from one side thereof and capable of being received in two respective corresponding recesses in the said joint portion, and with two flanges extending from the other side thereof, the flanges being for insertion in the bone. These flanges are preferably perforated, for the reasons explained in the preceding paragraph.

The whole of the humeral member and the implant portion of the ulnar member are preferably all of metal, and the joint portion of the ulnar member is preferably of a resilient plastics material. The metal used is preferably titanium or a chrome/cobalt alloy, since these are compatible with body tissue. The resilient plastics material used is preferably high-density polyethylene or a similar polymer.

The prosthesis according to the invention has the advantage of a smoothly operating pivotal joint with the two parts secured together in snap-fit engagement. With the humeral joint portion of metal and the ulnar joint portion of a resilient plastics material, the cooperating surfaces can work smoothly against each other without there being the difficulty of accurately machining two cooperating metal surfaces.

Figure 2:
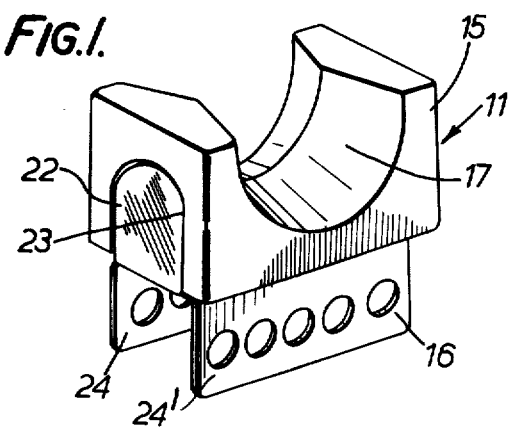
Figure 2:
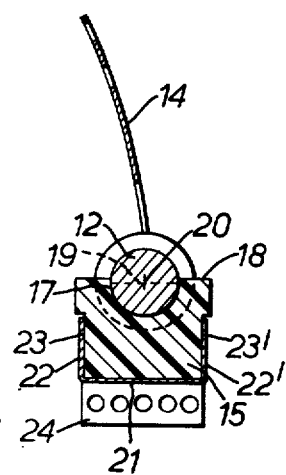

One form of elbow prosthesis according to the invention will now be described, by way of example only, with reference to the accompanying drawings, in which:

FIG. 1 is a perspective view of the prosthesis, with the humeral member and the ulnar member separated, and FIG. 2 is a vertical cross-section through the prosthesis, with the humeral member and ulnar member fitted together.

The prosthesis comprises a humeral member 10 and an ulnar member 11. The humeral member 10 comprises a substantially cylindrical joint portion 12 having a central annular neck portion 13 in the shape of two coaxial frustocones abutting at their smaller ends. A substantially V-shaped perforated laminar implant portion 14 is rigidly joined to the joint portion 12 and this laminar implant portion 14 is slightly curved (as can more clearly be seen in FIG. 2) in such a direction that a tangent to the curve extends substantially at right angles to the axis of the cylindrical joint portion 12. The whole of the humeral member 10 is of titanium.

The ulnar member 11 comprises a substantially cuboidal joint portion 15 of high-density polyethylene and an implant portion 16 of titanium. The joint portion 15 has a recess 17 for receiving the neck portion 13 in snap-fit engagement. The inner surfaces of the recess 17 conform to the surfaces of the neck portion 13. The cross-section of the recess 17 is substantially U-shaped and corresponds to the major segment of a circle, such that the top 18 of this joint portion 15 is slightly above the diameter 19 of the said circle. This diameter 19 passes through the pivotal axis 20, which is coterminus with the axis of the cylindrical joint portion 12. The implant portion 16 of the ulnar member 11 includes a base plate 21, with two lugs 22,22' extending from one side of this base plate 21 and being received in two respective recesses 23,23' on the joint portion 15. Two perforated flanges 24,24' extend from the other side of the base plate 21 for implantation in the bone.

What is claimed is:

1. A human elbow prosthesis having humeral and ulnar members with joint portions capable of fitting in a snap-fit engagement permitting the humeral member to pivot relative to the ulnar member and with implant portions capable of being rigidly fixed in bone without the use of cement, said prosthesis consisting essentially of:
   a. a humeral member of a metal compatible with body tissue having
      i. a substantially cylindrical joint portion with a central annular neck portion capable of being received in said snap-fit engagement with the joint portion of said ulnar member, and
      ii. a substantially laminar implant portion capable of being inserted into a humerus, said implant portion being rigidly secured to said joint portion and extending therefrom in a direction substantially at right angles to the pivotal axis of said prosthesis, said implant portion being perforated so that bone can grow through the perforations to insure rigid fixation thereof; and
   b. an ulnar member for receiving said humeral member, said ulnar member having
      i. a substantially cuboidal joint portion of a resilient plastic compatible with body tissue and having a complimentary recess for receiving the joint portion of said humeral member in said snap-fit engagement while permitting the humeral member to pivot relative to the ulnar member along a pivotal axis coincident with the longitudinal axis of said humeral joint portion; and
      ii. an implant portion of a metal compatible with body tissue comprising a base plate having means for attachment to said ulnar portion and a substantially laminar flange capable of being inserted into an ulna, said flange being perforated so that bone can grow through the perforations to ensure rigid fixation thereof.

2. A human elbow prosthesis according to claim 1, wherein the perforated laminar implant portion of said humeral member is substantially U-shaped or V-shaped in outline with the apex thereof insertable into the humerus and the base thereof rigidly secured to said joint portion.

3. A human elbow prosthesis according to claim 1, wherein the joint portion of said humeral member is defined by two coaxial frusto-conical portions abutting at their smaller ends.

4. A human elbow prosthesis according to claim 1, wherein the perforated laminar implant portion of said humeral member is slightly curved such that a tangent of said curve extends at substantially right angles to said pivotal axis.

5. A human elbow prosthesis according to claim 1, wherein the recess in said substantially cuboidal joint portion of said ulnar member extends from one side of said cuboidal shape through the opposing side thereof and is of substantially U-shaped cross-section in any plane parallel to said two sides.

6. A human elbow prosthesis according to claim 5, wherein the width of said cuboid shape between said two sides is substantially the same as the longitudinal axial length of the neck portion of said humeral member.

7. A human elbow prosthesis according to claim 5, wherein the depth of the recess in said ulnar member joint portion is slightly greater than the corresponding radius of the humeral member annual neck portion, such that the substantially U-shaped cross-section of said recess is the major segment of a circle.

8. A human elbow prosthesis according to claim 1, wherein the implant portion of said ulnar member comprises a base plate having two lugs extending from one side thereof for attachment to corresponding recesses in said ulnar joint portion and a pair of said flanges extending from the other side thereof for insertion into the ulna.

9. A human elbow prosthesis according to claim 8, wherein said lugs are at opposite ends of the base plate.

10. A human elbow prosthesis according to claim 1, wherein said metal compatible with body tissue comprises titanium.

11. A human elbow prosthesis according to claim 1, wherein said metal compatible with body tissue comprises a chromium/cobalt alloy.

12. A human elbow prosthesis according to claim 1, wherein the implant portion of said ulnar member is detachable from the joint portion thereof.

13. A human elbow prosthesis according to claim 2, wherein the joint portion of said humeral member is defined by two coaxial frusto-concial portions abutting at their smaller ends.

14. A human elbow prosthesis according to claim 7, wherein the implant portion of said ulnar member comprises a base plate having two lugs extending from one side thereof for attachment to corresponding recesses in said ulnar joint portion and a pair of said flanges extending from the other side thereof for insertion into the ulna.

15. A human elbow prosthesis according to claim 14, wherein the perforated laminar implant portion of said humeral member is substantially U-shaped or V-shaped in outline with the apex thereof insertable into the humerus and the base thereof rigidly secured to said humeral joint portion; and and joint portion of said humeral member is defined by two coaxial frusto-conical portions abutting at their smaller ends.

* * * * *